US006124937A

United States Patent [19]

Mittenzwey et al.

[11] Patent Number: 6,124,937

[45] Date of Patent: Sep. 26, 2000

[54] METHOD AND DEVICE FOR COMBINED ABSORPTION AND REFLECTANCE SPECTROSCOPY

[75] Inventors: Klaus-Henrik Mittenzwey; Gert Sinn, both of Berlin, Germany

[73] Assignee: Optosens Optische Spektroskopie und Sensortechnik GmbH, Berlin, Germany

[21] Appl. No.: 09/308,262

[22] PCT Filed: Nov. 14, 1997

[86] PCT No.: PCT/DE97/02718

§ 371 Date: May 12, 1999

§ 102(e) Date: May 12, 1999

[87] PCT Pub. No.: WO98/22802

PCT Pub. Date: May 28, 1998

[30] Foreign Application Priority Data

| | | | |
|---|---|---|---|
| Nov. 15, 1996 | [DE] | Germany | 196 47 222 |
| Jul. 18, 1997 | [DE] | Germany | 197 30 826 |
| Aug. 1, 1997 | [DE] | Germany | 197 33 253 |

[51] Int. Cl.[7] ..... G01N 21/00; G01J 3/42; G01J 3/427

[52] U.S. Cl. ..... 356/432; 356/319

[58] Field of Search ..... 356/432, 319, 356/435

[56] References Cited

U.S. PATENT DOCUMENTS

| | | | |
|---|---|---|---|
| 3,910,701 | 10/1975 | Henderson et al. | 356/39 |
| 5,125,742 | 6/1992 | Wilks, Jr. | 356/246 |
| 5,317,378 | 5/1994 | Mould et al. | 356/301 |
| 5,345,306 | 9/1994 | Ichimura et al. | 356/346 |
| 5,381,237 | 1/1995 | Sela | 356/436 |
| 5,459,566 | 10/1995 | Pearson et al. | 356/246 |

FOREIGN PATENT DOCUMENTS

| | | |
|---|---|---|
| 41 04 316 A1 | 9/1991 | Germany . |
| 41 24 545 A1 | 1/1992 | Germany . |
| 301 863 | 5/1994 | Germany . |
| 43 37 227 A1 | 5/1995 | Germany . |
| 195 26 943 A1 | 1/1997 | Germany . |
| WO 90/00732 | 1/1990 | WIPO . |

OTHER PUBLICATIONS

Bergmann et al., "Experimentalphysik", Polarisation und Doppelbrechung des Lichtes, pp. 468–471 (1993) (English summary of relevant parts).

Bergmann et al. "Experimentalphysik", Absorption der Strahlung, pp. 237–241 (1994) (English summary of relevant parts).

Schmidt, "Optische Spektroskopic" pp. (first page no number) 316–317 (1994) English summary of relevant parts).

(List continued on next page.)

*Primary Examiner*—Robert H. Kim
*Assistant Examiner*—Philip Natividad
*Attorney, Agent, or Firm*—Christie, Parker & Hale, LLP

[57] ABSTRACT

The invention relates to the synchronous determination of the absorption, fluorescence, dispersion and refraction of liquids, gases and solids (measurement volumes) with high sensitivity. Radiation of defined wavelength is coupled into a multiple reflection device. The transmitted coupling radiation is measured with a receiver that is located immediately behind a semireflecting mirror. The diffuse reflecting that is directed against the direction of incidence and the radiation which is specularly reflected at the boundary surface with the measurement volume are measured with a receiver that is directed at the measurement volume and located on the coupling mirror. The absorbing power is determined from the reciprocal value of the transmitted coupling radiation. The scattering power and fluorescence power are determined indirectly from the combination of diffuse reflection and transmitted radiation. The refraction is determined from the combination of specularly reflected radiation and transmitted radiation. The invention describes a method and a simple and robust device designed in modular system. Ranges of application are analysis, quality control and inspection in industry, environment and medicine.

30 Claims, 6 Drawing Sheets

OTHER PUBLICATIONS

Baumbach, "Luftreinhaltung", 5 Messtechniken zur Erfassung von Lufverunreinigungen, p. 178 (1992) German (English summary of relevant parts).

Kortum, "Reflexionsspektroskopie", pp. 106–109 (1969) (English summary of relevant parts).

Gerber, "Portable Cell For Simultaneously Measuring the Coefficients of Light Scaterring and Extinction for Ambient Aerosols" Item No. XP–002059096, Applied Optics, pp. 1009–1014, vol. 18, No. 17 (Apr. 1, 1979), U.S.

Mittenzwey et al., "MPSS: A New Scattering Technique for Sensitive Measuring of the Total Absorption of Fluids", Applied Spectroscopy, vol. 51, No. 2 (1997) U.S.

Colwell, "Manual of Remote Sensing" Remote Sensing Applications in Agriculture, p. 2141 (1983) U.S.

Mittenzwey et al. "A new Flourescence Technique to Measure the Total Absorption Coefficient in Fluids", Fresinius J. Anal Chem (1996) 354:159–162.

METHOD AND DEVICE FOR COMBINED ABSORPTION AND REFLECTANCE SPECTROSCOPY

FIELD OF THE INVENTION

The present invention relates generally to optical spectroscopy, and more particularly, to a method and device for combined absorption and reflectance spectroscopy.

BACKGROUND OF THE INVENTION

Spectroscopy is used for analytics, environmental control, quality control, and process control. Radiant energy is directed towards a substance and the absorption, diffuse reflection, dispersion, fluorescence, or refraction of the substance can be measured in order to determine the substance and its properties.

The prior art includes two major types of spectroscopy: (1) Absorption spectroscopy; and (2) Reflectance spectroscopy.

Absorption Spectroscopy

Conventional absorption methods are used for the detection of absorbing substances in measurement volumes, such as liquids, gases, or solids.

Radiation of a defined wavelength is coupled into the measurement volume. On its way through the measurement volume, the coupling radiation is attenuated by absorbing substances within the measurement volume. After a defined distance, the coupled radiation is again decoupled and directed to an optoelectronic receiver, which records the attenuated intensity I. The quotient of the attenuated and unattenuated intensity $I_o$ is the transmission T:

$$T=I/I_o=\exp(-\alpha_T\chi) \quad (1)$$

This law from Bouger-Beer-Lambert describes the relationship between transmission and the total absorption coefficient $\alpha_T$ (for the sake of simplicity dispersion has been ignored here). The term $\chi$ is the distance which the coupling radiation travels in the measurement volume. (BERGMANN and SCHAEFER: Textbook of Experimental Physics. Optics. Berlin-New York, Walter de Gruyter, 1993 and SCHMIDT, W.: Optical Spectroscopy. Weinheim-New York-Basel-Cambridge-Tokyo, VCH Verlagsgesellschaft, 1994.)

A special absorption method is based on the principle of evanescent wave fields or attenuated total reflection (ATR). Here, radiation is coupled into a light conducting solid, e.g., ATR crystal or an optical waveguide and after passing through a defined distance decoupled again. The optical waveguide is in contact with the measurement volume to be investigated. In the optical waveguide, the coupling radiation is totally reflected at the boundary surface with a measurement volume, whereby a small portion of the radiation penetrates into the measurement volume (evanescent wave) and interacts therewith. Thus, the coupling radiation is attenuated. This attenuation is measured. The classical relationship in Formula (1) applies. (BERGMANN and SCHAEFER: Textbook of Experimental Physics. Optics. Berlin-New York, Walter de Gruyter, 1993)

In the case of measurement volumes with very low optical densities (e.g., gases), the distance traveled by the coupled radiation in the measurement volume is increased in order to obtain evaluable signals. Long paths may be realized, for example, with the help of reflecting elements. (BAUMBACH, G.: Air Cleaning. Berlin-Heidelberg-New York, Springer Verlag, 1992) In DE 4104316A1, an internally reflecting spherical cell is introduced, in which the coupled radiation is reflected back and forth multiple times and then decoupled again and directed to a receiver. In DE 4124545A1, a gas absorption cell is described.

Recently, a method for the determination of total absorption has been proposed. Rather than measuring the coupling radiation attenuated after traveling a defined distance, the interaction radiation (fluorescence and dispersion) generated by the coupling radiation is measured. The special characteristic of this method is that the coupled radiation is almost completely absorbed by the measurement volume after a long path. (DD 301 863 A7. DE 43 37 227 A1, and MITTENZWEY, K.-H., J. RAUCHFUSS, G. SINN, H.-D. KRONFELDT: A new fluorescence technique to measure the total absorption coefficient in fluids. Fres. J. Anal. Chem., 354 (1996) 159–162 as well as MITTENZWEY, K.-H. & G. SINN: MPSS: A new scattering technique for measuring the total absorption in fluids. Appl. Spectr. 51 (1997) 2, 82–85)

Reflectance Spectroscopy

Reflectance spectroscopy combines diffuse reflection and specular reflection, i.e., directed reflection.

(a) Diffuse Reflection

Diffuse reflection R is the diffuse reflection of radiation on a material i.e., measurement volume. It is a measure of the intensity of the photons reflected opposite the direction of incidence. These are scattered photons in the classical sense. Diffuse reflection is determined by the dispersion power (dispersion coefficient $\beta$) and absorption power (total absorption coefficient $\alpha_T$) of the measurement volume. For the sake of simplicity, absorption will dominate in the following description of diffuse reflection. The theory of Kubelka and Munk is used for the mathematical description of diffuse reflection. In an infinitely extended measurement volume (e.g., a deep body of water), the diffuse reflection $R_S$ is proportional to the quotient of the dispersion coefficient and the absorption coefficient as follows.

$$R_S \sim \beta/\alpha_T \quad (2)$$

If the radiation incident in the measurement volume also generates fluorescence, the diffuse reflection is determined not only by the dispersion but also by the fluorescence power, which is characterized by the product of the fluorescence quantum yield $Q_F$ and the absorption coefficient of the fluorophore $\alpha_F$ of the measurement volume ($Q_F\alpha_F$) The fluorescence contribution $R_F$ to the diffuse reflection of extended measurement volumes is decisively controlled by the quotient shown in formula (3) below.

$$R_F \sim Q_F\alpha_F(\lambda_E)/[\alpha_T(\lambda_E)+\alpha_T(\lambda_F)] \quad (3)$$

where $\lambda_E$ and $\lambda_F$ are the wavelengths of the incident radiation and fluorescence, respectively. In many cases of transmitting measurement volumes, the absorption at the wavelength of the incident radiation is greater than the absorption at the fluorescence wavelength (e.g., eutrophic surface water), in which case, formula (3) changes to formula(4):

$$R_F \sim Q_F\alpha_F(\lambda_E)/\alpha_T\lambda_E) \quad (4)$$

Formulas (2) and (4) are characterized by the same mathematical structure. The diffuse reflection is in both cases first proportional to the dispersion or fluorescence power and also inversely proportional to the total absorption.

Diffuse reflection spectroscopy is used, for example, basically for remote sensing and is applicable to both very optically dense and transmitting measurement volumes.

Examples of optically dense measurement volumes include diffusion reflection measurements on vegetation (leaves or needles), to determine their physiological condition, or measurements on soils to determine moisture and structure.

Examples of transmitting measurement volumes include atmosphere, bodies of water, and oceans. Comparatively simple relationships are present when the incident radiation (global radiation, lidar) can die out in the measurement volume, e.g. in bodies of water, the incident radiation does not reach the bottom. KORTÜM, G.: Reflection spectroscopy. Berlin-Heidelberg-New York, Springer Verlag, 1969 and COLWELL, R. N.: Manual of remote sensing. Falls Church, The Sheridan Press, 1983.

(b) Reflectance

Reflectance spectroscopy is used preferably for the investigation of solid surfaces. In reflectance spectroscopy, the radiation directly reflected or directed from a surface is analyzed (reflectance law), which gives information concerning the spectral reflectance. In the analysis of diffuse reflection R from transmitting solid, liquid, and gaseous measurement volumes, the specular reflectance occurring at the boundary surface with the measurement volume is as a rule a disturbance variable, that is filtered out by suitable measurement arrangements.

The specular or directed reflectance $R_G$ is dependent, among other things on the refractive index n of the measurement volume. Since, in many cases, the measurement volume absorbs, the refractive index decisive for reflectance is also determined by the absorption power of the measurement volume. The refractive index $R_G$ is made up of a real component and an imaginary component (complex number):

$$R_G=((n-1)/(n+1))^2 \qquad (5)$$

with $n=n_{Real+nImaginary}$. The formula (5) is a simplified representation for the air/measurement volume boundary with perpendicular incident radiation. The refractive index is determined in practice goniometrically or interferometrically. (BERGMANN and SCHAEFER: Textbook of Experimental Physics. Optics. Berlin-New York, Walter de Gruyter, 1993 and SCHMIDT, W.: Optical Spectroscopy. Weinheim-New York-Basel-Cambridge-Tokyo, VCH Verlagsgesellschaft, 1994)

Advantages and Disadvantages of Absorption and Reflectance Spectroscopy

A significant advantage of classical absorption spectrometry compared to spectrometry measuring fluorescence and dispersion is that in classical absorption spectrometry, the coupled radiation falls directly on the receiver instead of indirectly on the receiver; thus, significantly more photons are available for measurement. High signal/noise ratios result from the large number of photons measured in classical absorption spectrometry. In classical absorption spectrometry, radiation sources with low photon fluxes and simple semiconductor receivers can be used because of the high signal/noise ratios. Consequently, the technical equipment outlay is relatively low. A significant disadvantage of classical absorption spectrometry is the relatively low sensitivity as a result of the exponential relationship between the coupling radiation attenuated by the measurement volume and the absorption coefficient, as shown in formula (1).

A significant advantage of diffuse reflection spectroscopy is that the relationship between the total absorption coefficient and the diffuse reflection is inversely proportional, as shown in formulas (2)–(4). Thus, diffuse reflection is more sensitive than the classical absorption spectrometry. Moreover, diffuse reflection includes information concerning the dispersion power and fluorescence power of the measurement volume. However, it is disadvantageous with diffuse reflection spectroscopy that the relationship between R and $\alpha_T,\beta,Q_F\alpha_F$ is ambiguous. This results in the fact that an exact separation of absorption power, dispersion power, and fluorescence power, respectively, is difficult and in many cases impossible. Moreover, the use of diffuse reflection for a sensitive determination of the absorption power of transmitting measurement volumes is bound to extended measurement volumes, since the radiation dies out only after relatively long paths in the measurement volume (e.g., 10–230 cm with typical absorption coefficients for surface water of from 1–23 $m^{-1}$). In samples with smaller layer thicknesses (e.g., classical cells), determining the absorption power is impossible. Furthermore, with the irradiation of light bundles with a finite cross-section in the extended measurement volume (e.g., lidar), the photometric distance law has a disruptive effect on the signal-to-noise ratio.

An advantage of reflectance spectroscopy is that the intensity of the radiation specularly reflected at the boundary surface with the measurement volume provides data concerning the refractive power, which is substance-specific. Using the refractive power, it is even possible to characterize substances which are completely incapable of absorption. However, it is disadvantageous that the specular reflectance also depends on the absorption power of the measurement volume and is thus ambiguous.

SUMMARY OF THE INVENTION

The object of the invention is to combine absorption spectroscopy and reflectance spectroscopy in a method and device such that all their advantages are combined and their disadvantages eliminated. Absorption, dispersion, fluorescence, and refraction of a measurement volume are determined synchronously in a single measurement procedure.

BRIEF DESCRIPTION OF THE DRAWINGS

These and other features, aspects, and advantages of the present invention will become better understood with regard to the following description, appended claims, and accompanying drawings where:

DETAILED DESCRIPTION

Figure 1:
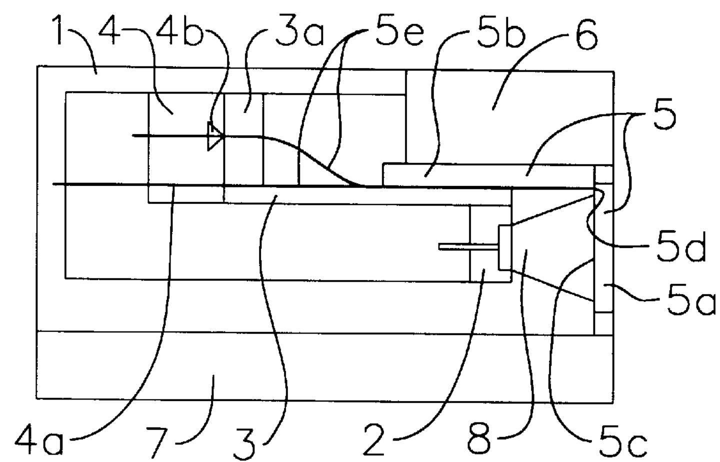
FIG. 1 shows the basic device for implementing the method for combined absorption and reflectance spectroscopy.

Spectroscopy is used to identify matter and/or its properties. A volume of matter is analyzed and optically measured. This measurement volume can be a liquid, gas, or solid. Radiant energy is directed towards the measurement volume and the absorption, diffuse reflection, dispersion, fluorescence, or refraction of the substance is measured in order to determine the substance and its properties.

In an exemplary embodiment of the invention, measurement volumes are located in a multiple reflection area covered by a coupling mirror and an opposing mirror. In another embodiment of the invention, measurement volumes are located outside the multiple reflection area and as a rule immediately on the edge or in the vicinity of the multiple reflection area.

Embodiments of the invention are first explained using the example of transmitting measurement volumes. Radiation with a defined wavelength is coupled into the measurement volume to be investigated. In an embodiment of the invention, the measurement volume is located between two opposing mirrors. The mirrors are designed such that through an adequately high number of reflections the path of the radiation coupled by the coupling mirror is long enough that it can be absorbed completely in the measurement volume. The complete absorption is a prerequisite for the development of diffuse reflection according to the formulas reported in the prior art (referred to here as saturated long-path diffuse reflection). Through multiple reflection, the requirement for extended measurement volumes is eliminated. Moreover, the photometric distance law no longer has a disruptive effect on the signal/noise ratio. The saturated long-path diffuse reflection is measured with a photoelectronic receiver aligned with the measurement volume and disposed on the coupling mirror in conventional diffuse reflection measurement geometry, i.e., at the back. The measurement signal is described according to Formula (2) in the case of dispersion and according to Formula (4) in the case of fluorescence.

A second significant measurement procedure occurs synchronously. The coupling mirror (or even the opposing mirror) is semireflecting, e.g., 10% transmission and 90% reflectivity. Consequently, after each reflection or after each cycle, a portion of the coupling radiation transmitted by the measurement volume passes through the coupling mirror and arrives at a second receiver disposed directly behind the coupling mirror. Ignoring the fluorescence and dispersion photons passing through the semireflecting mirror, the intensity $I_{Tr}$, of the transmitted radiation is described by the following formula in approximation:

$$I_{Tr} \sim m/\alpha_T \tag{6}$$

The term m is a characteristic and known constant for the transmittance of the coupling mirror. The total absorption coefficient aT can thus be determined directly from Formula (6). Compared to the classical absorption spectrometry (Lambert-Beer exponential law), Formula(6) is characterized by higher sensitivity, which results in lower detection limits and higher accuracy. With an increasing $\alpha_T$, $I_{tr}$ drops because with an increasing $\alpha_T$ the mean path length of the coupled radiation decreases until its virtually complete absorption in the measurement volume and thus the number of reflections or cycles drops. Thus, the intensity $I_{Tr}$ required of the coupling radiation passing through the semireflecting mirror also drops. Moreover, the intensity $I_{Tr}$ is also determined by the mirror constant m. The greater m is, the lower the reflectivity; or the greater the transmittance of the coupling, the higher $I_{Tr}$ is.

By inserting $\alpha_T$ in the Formulas (2) and (4), the dispersion power and fluorescence power, $\beta$ and $Q_F\alpha_F$, respectively, can be determined indirectly by taking into account a measurement of diffuse reflection. The ambiguity of the classical diffuse reflection spectroscopy is eliminated by combining diffuse reflection spectroscopy with absorption spectroscopy. For many applications, it will suffice to determine only the absorption power of the measurement volume by determining $I_{Tr}$ of Formula (6). In these cases, the diffuse reflection measurement can be eliminated, which results in a lower technical equipment outlay. A lower technical equipment outlay also results when the determination of the absorption power is not necessary and only the dispersion and fluorescence power is needed.

At the optical boundary with the measurement volume, specular reflection occurs if the contiguous media have different refractive indexes. Such a boundary can be glass/water, for example, whereby the glass serves as an optical window for the entry of the coupling radiation into the measurement volume. The intensity of the reflected radiation is recorded by a receiver. This intensity provides information concerning the refractive index of the measurement volume (Formula (5)). Since this refractive index is, in principle, complex, i.e. depends on the actual refractive index of the measurement volume as well as on its absorption power, a correction is performed. The refractive index determined from the reflected intensity is combined with the absorption coefficient determined from the transmitted radiation such that ultimately a refractive index (real component in Formula (5)) independent of the absorption of the measurement volume results. Thus, the ambiguity of the reflectance spectroscopy is eliminated by the combination of reflected intensity and the absorption coefficient.

Either the diffuse reflection is measured or dispersion and fluorescence are measured. The diffuse reflection is measured integrally in one application, i.e., a receiver without spectrally selective elements (e.g., filters) is aligned with the measurement volume. Dispersion and fluorescence are measured with two optoelectronic receivers and for the selective determination of the dispersion and fluorescence component of the diffuse reflection, filters to suppress the dispersion or fluorescence radiation are disposed upstream from the receiver aligned with the measurement volume.

The saturated long-path diffuse reflection is used for the correct determination of the absorption power to be determined from the transmitted coupling radiation. This solves a problem which occurs with dispersion or fluorescing measurement volumes in the determination of the absorption power using $I_{Tr}$ (Formula (6)). A receiver located immediately behind the coupling mirror records not only the coupling radiation transmitted by the measurement volume but also dispersion and fluorescence photons of the measurement volume. Consequently, the overall signal is thus greater than it would be if only the coupling radiation were recorded. As a result of the greater overall signal, according to Formula (6) smaller total absorption coefficients are simulated and a correction is thus necessary. The correction is subtracting an intensity which is proportional to the long-path diffuse reflection (dispersion or fluorescence) from the total intensity of the photons passing through the semireflecting mirror (direct coupling radiation plus dispersion or fluorescence). The proportionality factor is, among other things a function of the reflectivity and thus is a function of the transmission of the semireflecting mirror.

The dispersion and fluorescence power of the measurement volume can be determined directly. To measure the dispersion and fluorescence power of the measurement volume directly, the diffuse reflection (referred to here as short-path diffuse reflection) that originates from the part of the measurement volume located immediately behind the coupling point is measured. The coupled radiation can only travel a short path because the part of the measurement volume immediately behind the coupling point, which the diffuse reflection originates from, is small. The result is that a complete absorption of the coupling radiation does not occur in this part of the measurement volume. The relationship between diffuse reflection and dispersion power and fluorescence power is linear and independent of the total absorption coefficient. Dispersion power and fluorescence power may thus be determined directly using the linear short-path diffuse reflection. The quotient of this linear short-path diffuse reflection and the saturated long-path diffuse reflection moreover indirectly yields the absorption power or the total absorption coefficient. Thus, an additional independent value is available for comparison with the absorption coefficient determined with Formula (6), which also is very useful for corrections in the case of dispersing or fluorescing measurement volumes.

In an exemplary embodiment, the saturated long-path diffuse reflection and the linear short-path diffuse reflection are measured with time resolution, such as with the coupling of temporally very short pulses of less than 1 ns, for example. Their temporal widths are determined. The reciprocal of the difference of the temporal widths is a measure of the absorption power. This method has the advantage that different device-specific characteristics such as irradiation intensity, filter transmission, aperture, and radiation surface and receiver surface have no disruptive effect. The direct comparison between the saturated long-path diffuse reflection and the linear short-path diffuse reflection is possible without expensive correction.

The measurement of the linear short-path diffuse reflection is undertaken with a short time window and the measurement of the saturated long-path diffuse reflection is undertaken with a broad time window. The width of the two time windows to be adjusted is determined by the respective prevailing difference between the temporal widths of the short-path and long-path diffuse reflection based on the optical thickness of the measurement volume to be investigated.

In measuring the saturated long-path diffuse reflection and the linear short-path diffuse reflection, the diffuse reflection is first recorded time-integrally in a short time window (measurement of the linear short-path diffuse reflection) and also in a long time window (measurement of the saturated long-path diffuse reflection). Short paths in the measurement volume to be investigated are traveled by the coupled radiation in short times and long paths in long times i.e., short times are typical for the linear short-path diffuse reflection and long times for the saturated long-path diffuse reflection. The quotient from the short time window and the long time window is a measure of the absorption power of the measurement volume. This has the advantage that both diffuse reflections can be measured without great expense on purely electronic paths, which results in a robust structure and simple handling. The widths of the time windows to be set are implemented as a function of the measurement volume to be measured. In the case of optically thicker measurement volumes, the time windows are set shorter than with optically thinner measurement volumes. This results in correct measurement of saturated long-path diffuse reflections and linear short-path diffuse reflections as well as an optimization of the signal/noise ratios.

In another embodiment, spectrally selective elements for the coupling radiation and measurement radiation (filters, gratings) are adapted to the specific application and selected as follows. First, wavelengths which lie in the absorption ranges of the substances to be detected are used. Secondly, the wavelengths lie as much as possible outside these absorption ranges and are located at a characteristic absorption point of the solvent. In the first mode, the decision is made according to the measurement of absorption and diffuse reflection directly on the absorbing substance. The second mode makes use of the fact that the absorption of the solvent is reduced with the increase of the concentration of the substance to be detected. The measurement volume brightens as a result of this dilution effect at the absorption points characteristic of the solvent. This has the advantage that even substances which are completely incapable of absorption can be detected. The only prerequisite is the presence of a constant and well-defined absorption point of the solvent. In addition, spectrally selective elements may be arranged in which lie neither in the absorption range of the substance to be detected nor in the absorption range of the solvent.

Another embodiment is used for optically thin measurement volumes, which no saturated long-path diffuse reflections can be generated. No saturated long-path diffuse reflections can be generated since the wavelengths necessary for a virtually complete absorption of the coupling radiation cannot be generated with the use of simple multiple reflection devices. In this embodiment, diffuse reflection generated with optically thin measurement volumes is characterized by a linear relationship with the dispersion and fluorescence power and is independent of the total absorption coefficient (referred to here as linear long-path diffuse reflection). Thus, the dispersion and fluorescence power can be determined directly from the linear long-path diffuse reflection. Synchronously, the absorption power or the total absorption coefficient is determined, in that the radiation coupled into the measurement volume is decoupled out of the multiple reflection device after a defined number of reflections or cycles and directed to a receiver. The absorption power is thus determined not according to Formula (6), but rather classically according to the Lambert-Beer law (Formula (1)).

There is yet another embodiment for optically thin measurement volumes which likewise do not have adequately high minimum absorption such that no saturated long-path diffuse reflection can be generated as a result of multiple reflection. This embodiment determines the absorption power only by means of the coupling radiation transmitted through the semireflecting coupling mirror. Thus, changes (removal of mirrors, decoupling of the coupling radiation after traveling a defined distance) no longer need be made.

For the generation of saturated diffuse reflections and optimization of the signal/noise ratio in optically thin measurement volumes, artificial absorbers are used in the multiple reflection device or in the multiple reflection area. This results in a defined shortening of the path of the coupled radiation until its complete absorption. As a measure of the wavelength to be adjusted, the reciprocal of the smallest possible total absorption coefficient of the measurement volume is used. Artificial absorbers include, for example, gray filters. However, even the transmitting coupling mirror itself can act as an artificial absorber. The greater the transmittance of this semireflecting mirror, the shorter the mean path length of the coupled radiation until its complete absorption in the measurement volume. The mean path length is definitely influenced by the transmittance. Since the mean path length of the coupled radiation in the measurement volume is inversely proportional to the total absorption coefficient, it is possible to estimate the greatest possible mean path length from the knowledge of the smallest possible absorption coefficient of the measurement volume to be investigated and based on that to adapt the transmittance of the semireflecting layer of the coupling mirror.

This has the advantage that first the technical equipment expense for the production of multiple reflection units is reduced and, secondly, saturated diffuse reflections can be generated with a maximum signal/noise ratio independent of the optical thickness of the measurement volume.

Another embodiment is used with optically thicker (but still transmitting) measurement volumes. The number of cycles until the complete absorption of the incident radiation is small with thicker measurement volumes. The determination of the absorption power with higher sensitivity using the coupling radiation transmitted by the measurement volume and passing through the coupling mirror would be possible only to a limited extent according to Formula (6). Consequently, it is proposed to determine the absorption power using the classical method, in that either, instead of the opposing mirror, a receiver for the direct measurement of the coupling radiation attenuated by the measurement volume is used or the coupling mirror is removed and the receiver located immediately behind it is used for the measurement of the attenuated coupling intensity. The dispersion power and fluorescence power is determined from the linear short-path diffuse reflection.

Another embodiment is used when in the case of fluorescence, the absorption at the measurement or fluorescence wavelength can no longer be ignored (Formula (3)). The (fluorescence) diffuse reflection is then dependent on the absorption at the wavelength of the coupling radiation and of the fluorescence wavelength. The solution consists in that in addition to the measurement of the (fluorescence) diffuse reflection, the fluorescence is also measured at an angle of 90° relative to the coupling radiation. With a corresponding design of the multiple reflection cell, the 90° fluorescence is not dependent on the absorption at the fluorescence wavelength. The combination of (fluorescence) diffuse reflection, 90° fluorescence, and transmitted coupling radiation provides, first, the correct fluorescence power of the measurement volume and, secondly, the absorption at the measurement or fluorescence wavelength as well.

In yet another embodiment, the coupling radiation transmitted through the semireflecting coupling mirror and the diffuse reflection of the measurement volume are measured even in wavelengths ranges where, because of too little reflectivity of the semireflecting coupling mirror, be coupling radiation is no longer virtually completely absorbed by the measurement volume alone. The intensity curve of the coupling radiation on the path through the multiple reflection cell is also substantially determined by the mirror reflectivity. The lower the mirror reflectivity, the more sharply the intensity of the coupling radiation drops along its path. The saturation state is, based on its above definition, reached when the intensity of the coupling radiation drops to near zero on its path in the multiple reflection cell. This drop is caused here by the absorption of the measurement volume and by the mirror reflectivity of less than one acting as a loss component. The mathematical relationship between the intensity of the coupling radiation transmitted and the absorption power of the measurement volume is relatively more complex in structure compared to Formula (6), since device-related variables, such as the mirror reflectivity, also significantly affect the measurement signals. In principle, this relationship is still characterized in that it is, among other things, a function of the reciprocal of the intensity of the transmitted coupling radiation, i.e., the intensity of the transmitted coupling radiation drops with increasing absorption of the measurement volume. The relationship is unique. Consequently, the absorption power of the measurement volume can be determined from the coupling radiation transmitted. The diffuse reflection measured is likewise determined by the mirror reflectivity, by the absorption of the measurement volume, and by the dispersion power and fluorescence power of the measurement volume. In the case of the saturation state, the saturated long-path diffuse reflection develops. The diffuse reflection power is determined indirectly from the coupling of the measured intensity of the transmitted coupling radiation with the diffuse reflection signals.

The method for measurement volumes which have a sufficiently high minimum absorption such that saturated long-path diffuse reflection is produced as a result of the multiple reflection simply by the action of the measurement volume. In other words, the saturated long-path diffuse reflection is generated even with high mirror reflectivities (i.e., with a low effect of the mirror on the intensity behavior of the coupling radiation). The spectral reflectivity of the semireflecting mirror is tuned to the spectral absorption behavior of the measurement volume. In other words, knowing the anticipated spectral pattern of the absorption of the measurement volume, a mirror is used, whose wavelength ranges of high reflectivity coincide with the ranges of lower absorption of the measurement volume. Thus, it is ensured that the influence of mirror reflectivity on the intensity behavior of the coupling radiation along its path in the multiple reflection cell does not dominate such that the absorption of the measurement volume can be determined with adequately high sensitivity. On the other hand, the regions of low mirror reflectivities are used to cover the ranges of comparatively higher absorption of the measurement volume. In this case a greater influence of the mirror reflectivity is not all that disruptive of the determination of the absorption power of the measurement volume by means of the transmitted coupling radiation. This is illustrated using the example of drinking water. An interesting wavelength range for the investigation water extends from 250 nm to 750 nm. Perceptible absorptions appear as a rule in the UV range from dissolved organic matter. In the visible spectral range, the absorption drops sharply. There is no mirror which has a high reflectivity over the entire wavelength range of 250 nm to 750 nm and is also still semireflecting for the measurement of the transmitted coupling radiation. However, there are, for example, mirrors coated with silver, with comparatively high reflectivity in the visible spectral range (approximately 450 nm to 750 nm) and have significantly lower reflectivities in the short wave UV spectral range. Such a silver mirror is suitable for the investigation of water sense the wavelengths ranges of high mirror reflectivities coincide with the ranges of low absorptions of the water (visible range) and the ranges of lower mirror reflectivity coincide roughly with the ranges of greater water absorption (UV).

The spectral reflectivity of the semireflecting mirror is adapted to the spectral absorption of the optically thin measurement volume such that the wavelength ranges of high mirror reflectivity coincide with the wavelength ranges of comparatively high absorption of the measurement volume. Thus, it is achieved that the mirror reflectivity has a comparatively low influence on the intensity pattern of the coupling radiation and thus, nevertheless an adequately high measurement sensitivity can be realized. It is clear that the wavelength ranges of low mirror reflectivities are not very suitable for a sensitive measurement of the absorption of the management volume in the case of optically thin measurement volumes. In other words, with optically thin measurement volumes, the usable wavelength range is smaller than with measurement volumes which, as above, have an adequately high minimum absorption.

Another embodiment is a method which can be used on optically thick measurement volumes with which a saturated long-path diffuse reflection is generated even after very short travel distances of the coupling radiation in the measurement volume. If the measurement volume is located in the multiple reflection area between a coupling mirror and opposing mirror, the coupling radiation no longer reaches the opposing mirror, which is, consequently, also not further needed for the measurement procedure. Consequently, the opposing mirror designed as a convex mirror is replaced by an optically transmissive protective window whereby the measurement volume is located outside the multiple reflection area outside on the window. The radiation coupled into the measurement volume generates a diffuse reflection typical of the measurement volume, which reflection is controlled by the dispersion and absorption coefficients. The radiation diffusely reflected by the measurement volume falls on the semireflecting coupling mirror. Part of it is transmitted according to the mirror reflectivity; the rest, to the extent the mirror has negligible true absorption, is reflected back into the measurement volume, which, in turn, again diffusely reflects radiation in the direction of the semireflecting coupling mirror, and so on. The diffuse reflection transmitted through the semireflecting coupling mirror and/or the diffuse reflection falling on the diffuse reflection receiver (aligned directly with the measurement volume) is measured. This measurement procedure differs substantially from the classical diffuse reflection spectroscopy whereby the diffusely reflected radiation is measured right after the first reflection back from the measurement volume without multiple reflection. The advantage of the diffuse reflection measurement proposed here consists in that the interaction between photons and the measurement volume is substantially increased by the multiple coupling of the diffusely reflected radiation, which results in an increase in sensitivity. In addition, the multiple reflection may also be performed between a window provided with a substance-selective surface and the coupling mirror. The surface is located outside, whereby the measurement volume is brought into contact with this surface.

Moreover, a semireflecting mirror can be used instead of the window. The mirror coating of this opposing mirror is semireflecting such that nonreflecting regions, which act as optical openings, exist at defined locations of the mirror. These regions transmit part of the coupling radiation into the measurement volume. The rest of the coupling radiation is again reflected in the direction of the coupling mirror. In addition, interaction photons arrive out of the measurement volume into the sensor through the nonreflecting regions in the opposing mirror. The receiver located behind the coupling mirror records and intensity which depends on the diffuse reflectivity of the measurement volume.

The increase in sensitivity in the case of the window measurement becomes particularly noticeable with measurement volumes with diffuse reflectivities of, for example, more than 0.4. For example, bright powders (pharmaceutical industry) and paper (pulp-paper industry) are perceptibly diffusely reflecting. With lower diffuse reflections, this effect becomes smaller. Thus, for example, bodies of surface water are as a rule characterized by comparatively low diffuse reflections of approximately 0.05–0.1. The spectral reflectivity of the semireflecting coupling mirror and the spectral diffuse reflection of the measurement volume are tuned to each other, in that the wavelength ranges of high mirror reflectivity coincide with the wavelength ranges of higher diffuse reflections of the measurement volume and the wavelength range of lower diffuse reflections of the measurement volume coincide with the wavelength ranges of low reflectivities of the semireflecting coupling mirror. The method can (along with diffuse reflection) also be used for the investigation of thin films on surfaces (specular reflection).

In another embodiment, a new method for attenuated total reflection (=ATR) is introduced. Here, a light conducting solid (e.g., a modified ATR crystal) is brought between the coupling mirror and the opposing mirror. The radiation is coupled into the light conducting solid by the coupling mirror and travels long paths. The coupling radiation is resolved of the multiple reflection and is virtually completely absorbed. The measurement volume to be investigated is placed in contact with the solid (not on the coupling and decoupling surfaces, of course) such that the coupling radiation spreading in the solid reacts at the solid/measurement volume boundary with the measurement volume through evanescent radiation and is absorbed thereby.

The coupling radiation is absorbed as a result of long paths virtually completely in a light-conducting solid, whereby the measurement volume is in contact with the light-conducting solid such that the coupling radiation conducted through the solid can also be absorbed by the measurement volume through evanescent waves and the absorption of the measurement volume is determined from the reciprocal of the transmitted coupling radiation.

The transmitted radiation is recorded by the receiver located behind the semireflecting coupling mirror. The lower the radiation intensity transmitted, the greater the interaction of the coupling radiation with the measurement volume contacted at the boundary with the solid, i.e., the greater the absorption power. In contrast with classical ATR spectroscopy (Bouger-Beer-Lambert, Equation (1)), the relationship which applies here must be described by Equation (6). In other words, the complete absorption as a result of multiple reflection here again results in a significantly higher sensitivity. In addition to the transmitted radiation, the dispersion and the fluorescence can also, in principle, be measured. These diffuse reflections signals are used either, to the extent necessary, for the correction of the transmitted radiation relative to the fluorescence photons and dispersion photons passing through the semireflecting mirror and incident on the receiver located behind it, or for the determination of the absorption of the measurement volume.

In another embodiment, the radiation specularly reflected at the boundary surface with the measurement volume is measured and the refraction of the measurement volume is determined. Here, photons of a radiation source are directed at the boundary surface obliquely (i.e., at an angle differing from the axis of incidence). The boundary surface may, for example, be an optical window to a liquid. The radiation source, preferably, has small dimensions (e.g., point sources). The radiation falls on the optical window. Part of it is reflected both on the air/window boundary surface and on the window/measurement volume boundary surface of interest. The remaining part of the radiation penetrates into the measurement volume. The radiation source is imaged via a lens on a receiver located inside the angle of reflection. A lens may be disposed both in the incident beam and in the reflected beam. Two images of the radiation source develop in the imaging plane: (a) that through the air/window boundary and (b) that through the window/measurement volume boundary. The receiver is adjusted to the image through (b), since it alone contains information concerning the refractive power of the measurement volume. A good separation of the two images succeeds when oblique angles of incidence and adequately thick windows are used. Since (1) A specular reflection occurs at the boundary surface, (2) The optical image is adjusted to the plane of this boundary surface, and (3) Photons run out of the measurement volume in all spatial directions and the distance law $1/r^2$ applies to this, the share of photons diffusely reflected out of the measurement volume and incident on the receiver is small in comparison to the specularly reflected share. A correction relative to this disruptive diffusely reflected share can be, to the extent necessary, performed by means of the other receiver pointed directly at the measurement volume.

The combination of refraction at the boundary surface and diffuse reflection out of the measurement volume can also be advantageous and investigation of solid non-transmitting surfaces, of which, first, the properties of the solid phase (type, structure) and, second, the properties of the liquid or gaseous phases included in the solid phase are detected. An example of this is the investigation of masonry (moisture and state).

Another embodiment deals with measurement volumes whose refractive index changes only a little or not even measurably. That is the case, for example, for solvents with substances in the mg/1 range and lower. A very widespread solvent is water (surface water, wastewater, etc.). If water comes into contact with the optical window of a sensor, it can cause deposits (e.g., lime, algae, bacteria). The diffuse reflection passed through the window and the transmitted coupling radiation can be altered by this. Erroneous conclusions concerning the measurement volume to be investigated result. Deposits on the window/water boundary result in a change of the intensity of the radiation specularly reflected at the boundary surface, which is used as a measure of the disruptive change in the optical characteristics of the window. This measure is used for the correction of the diffuse reflection as well as the transmitted radiation.

In principle, the refraction must also be taken into account with multiple reflection, since reflections of specularly reflected radiation develop on the optical boundary. These reflections should not reach the diffuse reflection receiver if at all possible. Consequently, the diffuse reflection receivers are disposed outside the direction of reflection. The specularly reflected coupling radiation strikes a light trap for its complete elimination. An additional receiver may be used to measure the specularly reflected intensity instead of using a light trap, since the specularly reflected coupling radiation includes data about the refractive power of the measurement volume. The refraction of the measurement volume is determined by means of an evaluation algorithm. This evaluation algorithm eliminates device-specific characteristics and the minds the spectrally reflected intensity with the intensity of the coupling radiation transmitted through the semireflecting mirror, to determine the real portion from the complex refractive index.

Another embodiment is a method whereby the rate of flow of moving measured volumes is determined from their diffuse reflection. For this, two diffuse reflections different relative to time are determined.

First, an integral diffuse reflection, which depends both on the inherent absorption, dispersion, and fluorescence power and the refractive power and also on the rate of flow of the measurement volume, is determined within a fixed predefined, comparatively large time interval. Note: In the special case of refraction, specular reflection occurs instead of diffuse reflection. Secondly, a differential diffuse reflection, which depends exclusively on the inherent absorption, dispersion, and fluorescence power as well as refractive power of the management volume, is determined within a comparatively short time interval. The time dependency of the differential diffuse reflection is generated in that the diffuse reflection is determined in a very short time interval. This results in the fact that at the time of the detection of the measurement value, the measurement volume column flowing passed the receiver is virtually at rest. The combination of the integral and differential diffuse reflection yields a parameter which depends solely on the rate of flow. In detail, the rate is determined as follows. The number of all diffuse reflection pulses detected by an optoelectronic receiver during a defined time interval is determined. These pulses originate from the particles or structures of the measurement volume. The sum of the pulses (integral diffuse reflection) is proportional to the number of particles which pass by the receiver. This particle number is dependent on the particle concentration (~distance between particles) and on the rate of flow. The particle concentration is determined from the inherent absorption, dispersion, and fluorescence power as well as the refractive power of the measurement volume by means of the time-dependent differential diffuse reflection. This yields a unique relationship with the rate of flow: The more particles that flow past the receiver within a defined time, the greater their speed must be. A different method consists in determining the integral diffuse reflection of individual particles during their dwell time in the active zone considered and viewed by the receiver. During this time, the diffuse reflection is "integrated onto" the particles. This diffuse reflection is dependent on the diffuse reflectivity of the measurement volume or the particles and on the particle speed. The diffuse reflectivity is again determined from the inherent absorption, dispersion, and fluorescence power as well as the refractive power by means of the time-independent differential diffuse reflection. This yields a unique relationship with the rate of flow: The greater the diffuse reflection integrated onto the particle, the greater the dwell time of the particle in the active zone has to be. The dwell time is inverse to particle speed. This dwell time may also be determined as follows. For this, the particle pulse is measured with time resolution and its average with each used as a direct measure of the dwell time of the particle in the active zone (the extent of what is likewise known). The pulse width is, in other words, the diffuse reflection integral normed to the diffuse reflectivity of the particle.

Moving measurement volumes with rotating elements constitute a special case. A rapidly moving liquid can develop vortexes. The rotational speed of the vortexes greatly influences the cross-section of the vortex and its position in the liquid column (meander). Assuming known hydraulic conditions (e.g., constant, known input), the rotational speed is determined by optoelectronic observation (camera) and determination of the position of the vortex.

In the following, a device for performance of the method is described.

In FIG. 1, the absorption module 1 is illustrated. This is made up of the coupling module 5, the measurement module 2, the optical waveguide module 3, and the connection module 4. The absorption module is also the carrier for the module for the measurement of diffuse reflection 6 and refraction 7. The coupling module is used first to couple radiation into the measurement volume (coupling radiation). The coupling radiation is then reflected a plurality of times between reflecting elements, for which a reflection module is placed opposite the absorption module (for the various embodiments of the reflection module, see below). Secondly, the coupling module is used to couple radiation back into the sensor (coupling radiation transmitted through the semireflecting mirror 5*a*). The coupling module consists of the coupling mirror 5*a* and the optical waveguide block 5*b*. The coupling mirror is preferably planar; but may also be designed as a sphere for specific applications. The coupling mirror or its mirror substrate (e.g., glass) is coated with a semireflecting coating 5*c*, which, for example, transmits 10% radiation and reflects 90% (ignoring the absorption of the coating). This coating is applied on the inward facing side of the mirror pointing in the direction of the measurement module 2. This has the advantage that this reflecting coating is protected by the glass substrate from the outside against environmental influences; an additional protective coating is thus not necessary. The block 5*b* includes a plurality of optical waveguides 5*e*, which are densely glued to each other. The diameters of the optical waveguides are small compared to diameter of the coupling mirror. The optical waveguides are aligned parallel to the normal of the coupling mirror. The end faces of the optical waveguides are located in a straight line and form a common vertical plane. The end face of the block 5*b* also lies in this plane. This light waveguide plane lies flat from the inside against the upper region 5*d* of the coupling mirror. This region is nonreflecting. In this region, the coupling mirror is transmissive to the radiation coupled into the measurement volume. The mirror coating and light waveguide and faces form a common particle plane. Immediately behind the coupling mirror is located a radiation guiding volume, which is designed, for example, as an inside mirrored conic reflector 8, which guides the coupling radiation passing through the coupling mirror to the measurement module 2 with the optoelectronic receiver attach there. The receiver records (in addition to diffuse reflection photons) the intensity of the coupling radiation transmitted, whose reciprocal is a measure of the absorption of the measurement volume. The optical waveguide module 3, which accepts the optical waveguides from the optical waveguide block 5*b* and forwards them to specifically defined points in the block 3*a*, is disposed upstream from the coupling module. There, the optical waveguides are fixed, for example, by gluing into holes provided therefor. The planar end faces of the optical waveguides lie in a common vertical plane. The end face of the connection module 4 also lies in this plane. This connection module, which is disposed upstream from the optical waveguide module 3, has the function of providing the optical waveguide module radiation to be forwarded. A plurality of light emitting diodes (LEDs) 4*b* and an optical waveguide 4*a* are located there. The optical waveguide is used to conduct radiation of an external source, which is connected to the sensor by a SMA connection. Spectrally selective elements may also be disposed between the sensor and external radiation source. The end faces of the LEDs and that of the optical waveguide lie in a common vertical plane. The end face of the connection module 4 also lies in this plane. Instead of LEDs, optical waveguides, which run to the outside, may also be located here. The arrangement described has, because of its modular design, the advantage of being simple to adapt to the measurement conditions on site and to enable simple manufacture.

Various types of reflection modules may be combined with the absorption module. The arrangements thus possible result in the fact that the measurement volume can be located either inside the multiple reflection area between the coupling mirror and the opposing mirror or otherwise located outside it. It can also be unaffected by such a volume, i.e., the measurement volume is not located in a radiation guiding volume.

Figure 4:
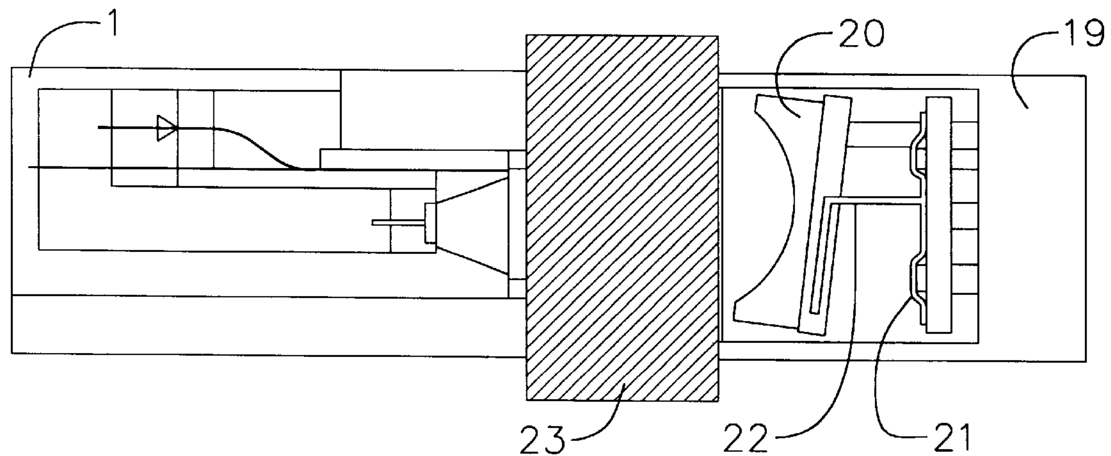
FIG. 4 shows a reflection module equipped with a concave mirror.

The optical waveguides located in the coupling module are disposed in the immediate vicinity of the mirror coating. The end faces of the optical waveguides are located indirectly above the mirror coating 5*c*. This facilitates the optical adjustment significantly and generates less loss of coupling radiation during the multiple reflection in the case that the reflection module is equipped with a concave mirror as shown in FIG. 4.

The conical reflector 8 disposed immediately behind the coupling mirror 5*a* also acts as a cross-section converter for the coupling radiation passing through the coupling mirror. Its diameter on the mirror side corresponds to the diameter of the reflecting layer of the coupling mirror and its diameter on the receiver side corresponds to the light sensitive surface of the receiver in the measurement module 2. The diameter on the mirror side of the cone is greater than the diameter on the receiver side. Thus, receivers may be used whose dimensions are adequately small not to disrupt the positioning of the optical waveguides in the coupling module 5 and the optical waveguide module 3 but nevertheless are capable of recording the total transmitted coupling radiation. An optical waveguide, which is run to the outside, instead of the receiver may be located in the measurement module. If necessary, a dispersion or diffuser plate can be disposed between the coupling mirror and the optical waveguide to reduce directed radiation.

The LEDs located in the connection module are planar in the emission direction. The original LED dome is shortened so that the distance between the emitter and the emission surface is as small as possible. The emission surface is polished for maximum radiation transmission.

The end faces of the connection module 4 and the optical waveguide module 3*a* lie flat against each other. The optical waveguides 5*e* in the optical waveguide module and the LEDs as well as the one optical waveguide 4*a* in the optical waveguide module are positioned such that the light conducting end faces located in the in the optical waveguide module are centered with those in the connection module and closely opposite them. This ensures maximum radiation transmission from the connection module to the optical waveguide module.

The transmitted coupling radiation and also diffuse reflection photons passing through the coupling mirror are controlled by spectrally selective elements (e.g., bandpass filters or cut-off filters). Spectrally selective elements are disposed between the coupling there are and measurement module. This is advantageous, for example, in the case of the coupling of white light. The coupling radiation transmitted, which is also white, can then be spectrally resolved (e.g., by means of a polychromator, which receives the transmitted coupling radiation via an optical waveguide).

In addition, instead of the coupling mirror, a protective glass and/or a filter may be put in place. The sensor then operates as a conventional absorption spectrometer, whereby the reflection module (see embodiments below) serves to lengthen the path of the coupling radiation. With optically thick measurement volumes, the sensor is operated in without the reflection module and is, this case, a classical diffuse reflection spectrometer.

Spectrally selective elements for the coupling radiation and measurement radiation (LEDs, filters, gratings) are adapted to the respective application and designed as follows. First, the sensor wavelengths are in the absorption region of the substances to be detected. Secondly, these are located outside this absorption region, and, as much as possible, disposed at a characteristic absorption point of the solvent. In the first mode, a conclusion as to the absorbing substance is made directly after the measurement of absorption and diffuse reflection. The second mode makes use of the fact that in the absorption of the solvent is reduced with the increase of the concentration of the substance to be detected. The measurement volume brightens as a result of this dilution effect at the absorption points characteristic for the solvent. This has the advantage that it is possible to detect even substances which are completely incapable of absorption. A prerequisite is merely the presence of constant and well-defined absorption point of the solvent. In addition spectrally selective elements which lie neither in the absorption region of the substances to be detected nor in the absorption region of the solvent.

Figure 2:
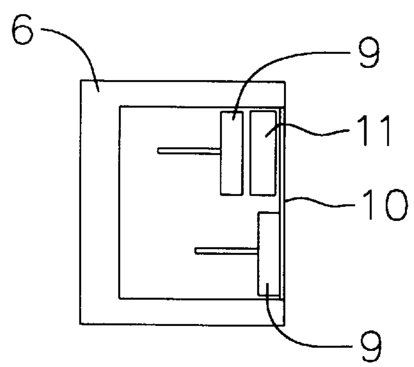
FIG. 2 shows the diffuse reflection module.

The diffuse reflection module 6 is disposed at a minimum distance from the optical waveguide of the coupling module (FIG. 2, top view). Its optical window 10 and the coupling mirror of the absorption module lie in a common plane. It is thus guaranteed that the diffusely reflected radiation is shadowed little or not all by the extensions of the sensors, which protrude into the beam path between diffuse reflection photons and the diffuse reflection receiver. The window of the receiver may already serve as a protective window for the diffuse reflection module. The diffuse reflection module may also be equipped with two receivers 9, whereby the first records the dispersion and the other the fluorescence (cut-off filter 11 in front of the receiver). The two receivers may also be disposed such that the areas a defined between the two distance. This is necessary if, as a result of the action of an imaging opposing mirror, the radiation specularly reflected from optical boundary surface is falls completely into the space between the two receivers. The receivers record only the diffuse reflection of the measurement volume. In addition, another receiver, which records both specularly reflected radiation and diffuse reflection, may be located between the two diffuse reflection receivers. Optical waveguides, which are run outward, may also be placed instead of the receivers.

On the other hand, it is possible, with a diffuse reflection receiver shifted downstream by a defined distance adapted to the application, in particular with optically thicker measurement volumes for the diffuse reflection by the above-mentioned shadowing to be intensified, in the effect of the distance law $1/r^2$ in his not too great.

For the measurement of a linear short-path diffuse reflection, the diffuse reflection module is outfitted with optics pointed directly at the coupling site.

Figure 3:
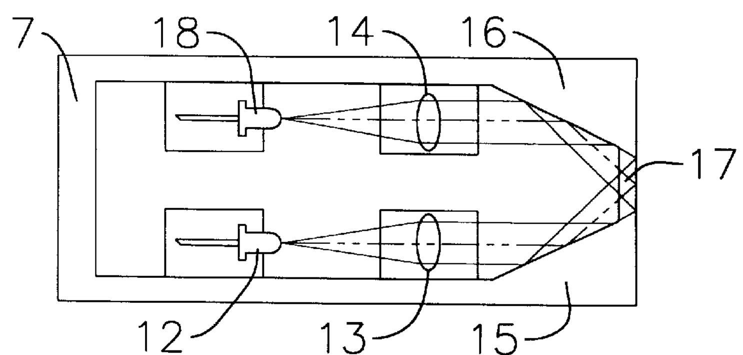
FIG. 3 shows the refraction module.

Radiation is generated in the refraction module 7, e.g., using an LED 12. The refraction module is depicted in FIG. 3. The LED is imaged by collecting lenses 13, 14 on a receiver 18, e.g., in the scale 1:1. The radiation is reflected onto the optical window 17. Reflecting elements 15, 16 (e.g., aluminum mirrors) are located in the beam path of the incident light beam and in the beam path of the reflected light beam. Thus, first, an adequately long path of the LED radiation and, secondly, an oblique of radiation on the optical window are achieved. A long path or an adequately great distance between the receiver and the measurement volume is necessary for the reduction of the diffuse reflection photons originating from the measurement volume and falling on the receiver. Thus, the receiver records primarily radiation specularly reflected at boundary surfaces. An oblique incidence of the LED beam on the window increases the separation sharpness between the reflection of interest at the window/measurement volume boundary surface and the unwanted reflection at the air/window. The number of the use reflection photons incident on the receiver becomes even smaller with a smaller receiver surface. For a high signal/noise ratio, it is advantageous to implement be aforementioned 1:1 imaging of a small emitting surface, e.g., the emitter of an LED. Expediently, the optical window of the refraction module is disposed in a common plane with the coupling mirror. Instead of the radiation source and the receiver, it is also possible to place optical waveguides, which run to the outside.

FIG. 4. depicts a case in which the measurement volume is located between the planar coupling mirror and a concave opposing mirror 20. The optical guidance of the coupling beam is in implemented by means of the imaging concave mirror. The multiple reflection takes place between the coupling mirror and the concave mirror. The measurement volume may be of various types: classical cell filling, flow through, or free stream. A concave mirror 20, which can be varied either with regard to its distance from the coupling mirror is mounted in the reflection module 19 or with regard to the tilt angle of its mirror plane using leaf springs 21, 22 by means of adjustment screws. The concave mirror is adjusted relative to its distance such that the end faces of the optical waveguide are located between one and two times the focal distance. With regard to its tilt angle, the concave mirror is adjusted such that with a mirror distance, which corresponds to twice the focal distance, the images of the end faces of the optical waveguide (image scale 1:1) is located in the lower region of the coupling mirror. The lower region is the region of the coupling mirror opposite the optical waveguides (i.e., the end faces of the optical waveguides are located above—their images below, whereby the images lie on the mirror coating!) Such an arrangement enables a readily executable adjustment procedure to achieve efficient multiple reflection of the coupling radiation. In special applications, the mirror distance it is equal to the focal distance of the concave mirror. Applications, e.g.: Transparent liquids in the petroleum, textile, food, and chemical industry.

For the case in which the external conditions of sensor mounting and complex sensor requirements do not permit tilting of the concave mirror, then the mirror is adjusted by vertical shifting instead of tilting.

Figure 5:
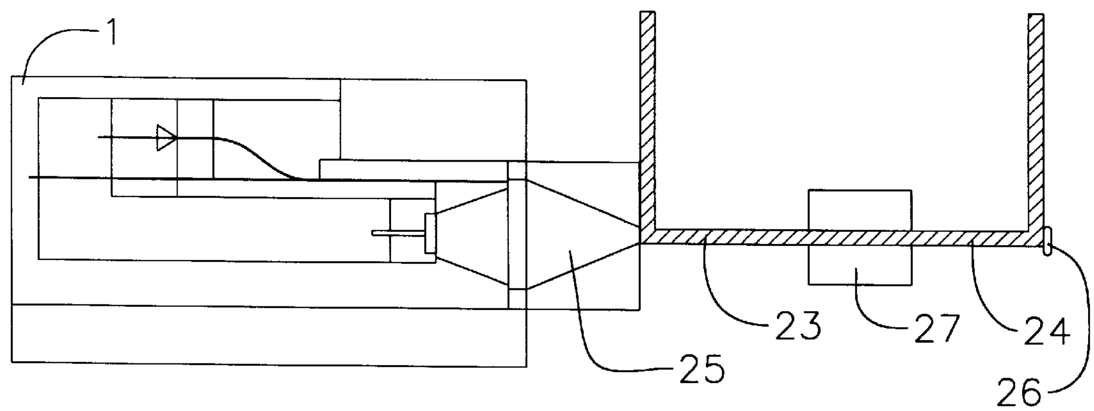
FIG. 5 shows an embodiment in which the measurement volume is located between the coupling mirror and the opposing mirror in a radiation guiding volume.

FIG. 5 shows application of an embodiment in which the measurement volume 23 is located between the coupling mirror and the opposing mirror in a radiation guiding volume. The diffuse reflection module and the refraction module are in operation that the time or not depending on the application. The opposing mirror 26 is a full planar mirror. The radiation guiding volume 24 may, for example, be an HPCL flow-through capillary which guides the coupling radiation. The multiple reflection occurs between the coupling mirror and the opposing mirror and capillary. If need be, a light guiding cone 25 to guide the coupling radiation is disposed between the coupling module and the optical and face of the capillary facing it, the diameter of the capillary side of the cone matches that of the capillary. The opposing mirror may be disposed separately or vapor deposited onto the other end face of the capillary. Instead of a rigid capillary it is also possible to place a flexible, hollow, liquid guiding optical waveguide. In addition, an optoelectronic receiver 27 may be mounted such that it records the interacting photons generated at an angle of 90° to the incident radiation, such as fluorescence and dispersion. Applications include, for example transparent liquids in flow-through measurements, HPCL lab analytics.

Figure 6:
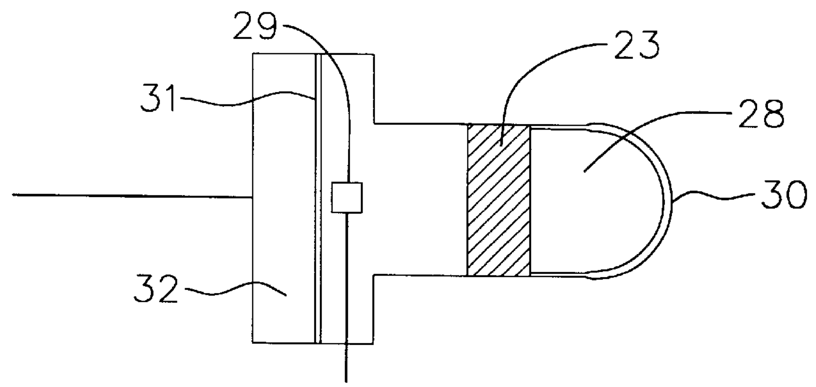
FIG. 6 shows an embodiment, which includes an LED, wherein an LED dome has no opening for the measurement volume.
Figure 7:
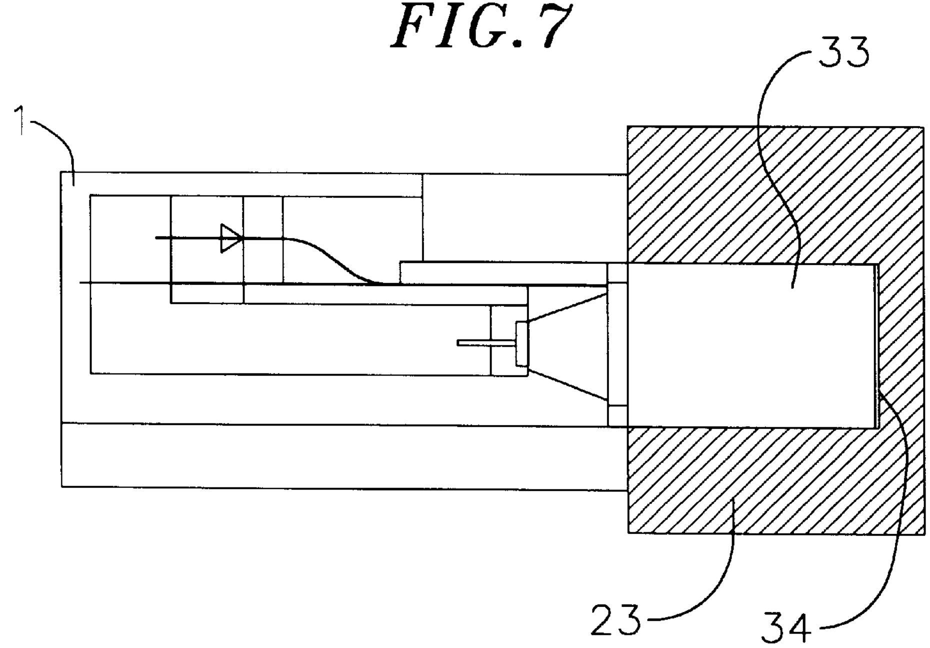
FIG. 7 shows an embodiment that has the measurement volume located outside the sensor.

In another embodiment in which the measurement volume 23 is located between the coupling mirror and the opposing mirror in a radiation guiding volume, the end face of the coupling 29 is disposed immediately upstream from the coupling mirror 31 as shown in FIG. 6. The measurement module 32, i.e., the optoelectronic receiver is located directly downstream from the coupling mirror. Such a device can be readily realized with a radiation guiding element, such as a commercially available LED 28. The electrical connectors of the LED are run out on the side. This provides an adequate surface for the deposition of semireflecting mirror coating 31 on the LED base. The receiver 32 is glued, for example, directly on the LED base. The coupling mirror may also be located in a different place. For this, the LED dome is separated immediately upstream from the LED emitter, the coating for the coupling mirror vapor deposited on the inside surface, and the two parts reassembled. The semireflecting coating then includes a small optically transmissive opening for the coupling of the emitter radiation. On the face opposite the semireflecting coupling mirror, the opposing mirror 30 is vapor deposited. The opposing there are may be designed concave or planar. The multiple reflection occurs by means of the coupling mirror and the opposing mirror. The LED element (dome) can be used for radiation guidance as a result of total reflection. The dome may also be mirrored from the outside. The measurement volume 23 is located in an opening between the coupling mirror and the opposing mirror. The size of the opening is adapted to the optical characteristics of the measurement volume to be investigated. To produce different wavelengths, multiple LEDs are placed.

A further modification consists in the fact that no mirror coatings are applied as coupling mirror and opposing mirror. If, in this case, an additional receiver is installed on the side opposite the emitter, the LED is a simple absorption and diffuse reflection spectrometer, whereby multiple LEDs are placed to produce different wavelengths.

The arrangement of multiple LEDs can be linear or in a drum, for example. Here is useful to bring the emission forward (absorption) and back (diffuse reflection) to a receiver via an optical device. In this case, the LEDs are controlled at different times in flashing operation. Another possibility consists in actuating the LEDs simultaneously and performing the imaging on a diode array or a CCD camera.

There is another embodiment where the measurement volume is located outside the sensor (i.e., the measurement volume is located outside the multiple reflection area equipped with the coupling mirror and the opposing mirror), the multiple reflection take place between the planar designed coupling mirror 5*a* of the coupling module, the opposing mirror 34, and a radiation guiding element 33 located between the two mirrors, which element may be, for example, an ATR crystal. The opposing mirror is a full, planar mirror. The coupling radiation is guided into the ATR crystal. The interaction between the coupling radiation and the measurement volume 23 located outside on the ATR crystal takes place by means of the evanescent wave fields existing in the immediate vicinity of the crystal. The ATR crystal may also be coated with a substance selective coating. If need be, a radiation guiding cone to adapt the diameter of the coupling mirror and the ATR crystal may be disposed between the coupling mirror and the ATR crystal. Instead of the ATR crystal, a flexible optical waveguide may also be placed. The refraction module is in operation and in contact with the measurement volume. The diffuse reflection module is usually not in operation. By means of a special flanging of the ATR crystal such that one portion of the end face of the optical waveguide in the coupling module couples radiation into the measurement volume and another portion couples radiation into the ATR crystal, the diffuse reflection module may also be in operation. With this arrangement, absorption, diffuse reflection, and refraction can be measured synchronously, for example, in extremely cloudy measurement volumes. Applications, e.g.: Industrial wastewaters.

Figure 8:
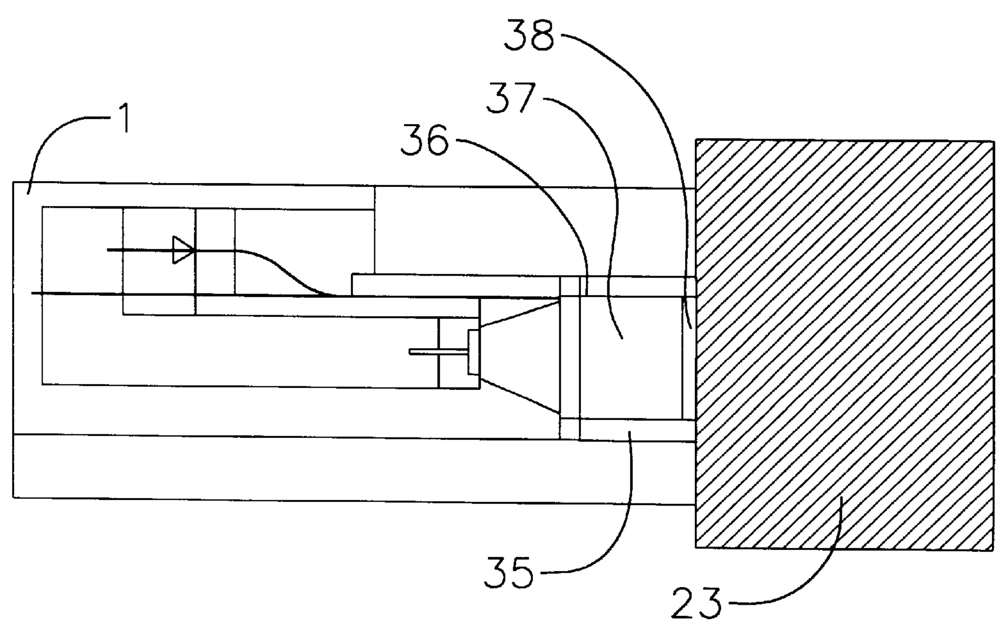
FIG. 8 represents embodiments that have the measurement volume located outside the sensor and instead of an opposing mirror, it either includes an optical window 38 or an opposing mirror 38 with transmissive regions located on the measurement volume.

Other embodiments have the measurement volume located outside the sensor as shown in FIG. 8. Instead of an opposing mirror, as considered to this point, in one embodiment there is an optical window 38 and in another embodiment, there is an opposing mirror 38 with transmissive regions located on the measurement volume 23.

In the embodiment with the optical window, a radiation guiding volume 37 is disposed between the measurement volume or window and the coupling mirror. After radiation through the optical waveguide block 5*b* of the coupling module, multiple reflection between the measurement volume, the coupling mirror 5*a*, and the radiation guiding volume 37. This volume may be an internally mirrored hollow element and/or a solid guiding radiation by means of total reflection. The form of the radiation guiding volume may vary. For example, the form of the radiation guiding volume may be cylindrical or conical. The sensors are set centrally 35, 36 on the measurement volume 23. This seating for the measurement volume bonding is a solid body or block. If need be, the diffuse reflection module and the refraction module may be in operation and be placed on the measurement volume. In this case, the diffuse reflection module and the refraction module are shifted forward compared to FIG. 1 in the direction of the measurement volume and themselves form the seat for the measurement volume bonding. The window 38 in contact with the measurement volume is optically transmissive. The radiation guiding volume between the coupling mirror and a window may also be a flexible optical waveguide. This may be disposed in a bundle depending on the application with additional optical waveguide of the diffuse reflection module and the refraction module. The sensor may also be designed without a window, for example, with solid surfaces. If the radiation guiding volume 37 is a solid guiding radiation by means of total reflection, its surface on the measurement volume side is identical with the window. Applications are, among others, measurement volumes with comparatively high diffuse reflectivity, such as milk and paper.

Moreover, a semireflecting mirror 38 may be placed instead of the window. The multiple reflection of the coupling radiation takes place in the radiation guiding space 37 between the coupling mirror 5*a* and the opposing mirror 38. The mirror coating of the opposing mirror is semireflecting such that nonreflecting regions, which act as optical openings, exist at specific locations of the mirror. These regions transmit part of the coupling radiation into the measurement volume. The other part of the coupling radiation is reflected back in the direction of the coupling mirror. In addition, interaction photons from the measurement volume arrive through the nonreflecting regions in the opposing mirror into the sensor. The receiver located behind the coupling mirror records an intensity which depends on the diffuse reflectivity of the measurement volume. Example applications are: Measurement volumes with comparatively low diffuse reflectivity, such as surface waters, wastewaters, and water leached from landfills.

In an embodiment with an optical window 38, the optical window may be coated with an indicator or a substance selective layer, which is in contact with the measurement volume. This window may also be mechanically roughened or have mechanical structures with a defined pore size. The pores act as a substance selective surface, for example for the separation of liquid substances from solid particles. Similarly, the opposing mirror may be equipped at its optical openings with an indicator or a substance selective layer or surface, which interacts with the measurement volume.

Figure 9:
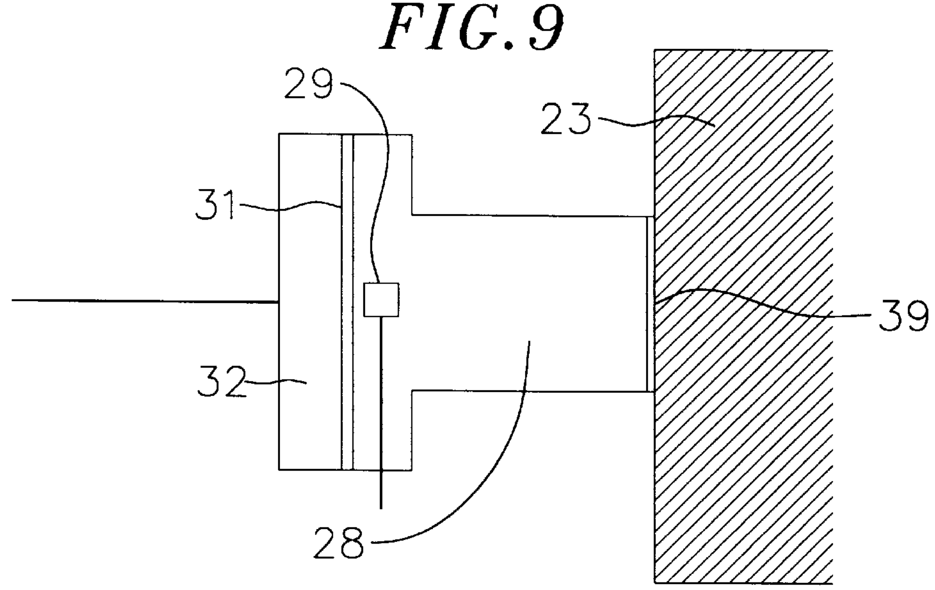
FIG. 9 shows an embodiment, which includes an LED, the LED dome having no opening for the measurement volume.

In another embodiment, which includes an LED, the LED dome 28 has no opening for the measurement volume. FIG. 6 shows an LED with an opening for the measurement volume, whereas FIG. 9 shows no opening for the measurement volume. The measurement volume 23 is located outside. The surface of the LED 39 opposite the coupling mirror 31, which may be either planar or originally convex, has the function of the window or that of the opposing mirror with transmitting regions. The dome is used for beam guidance and may be mirrored if need be.

Figure 10:
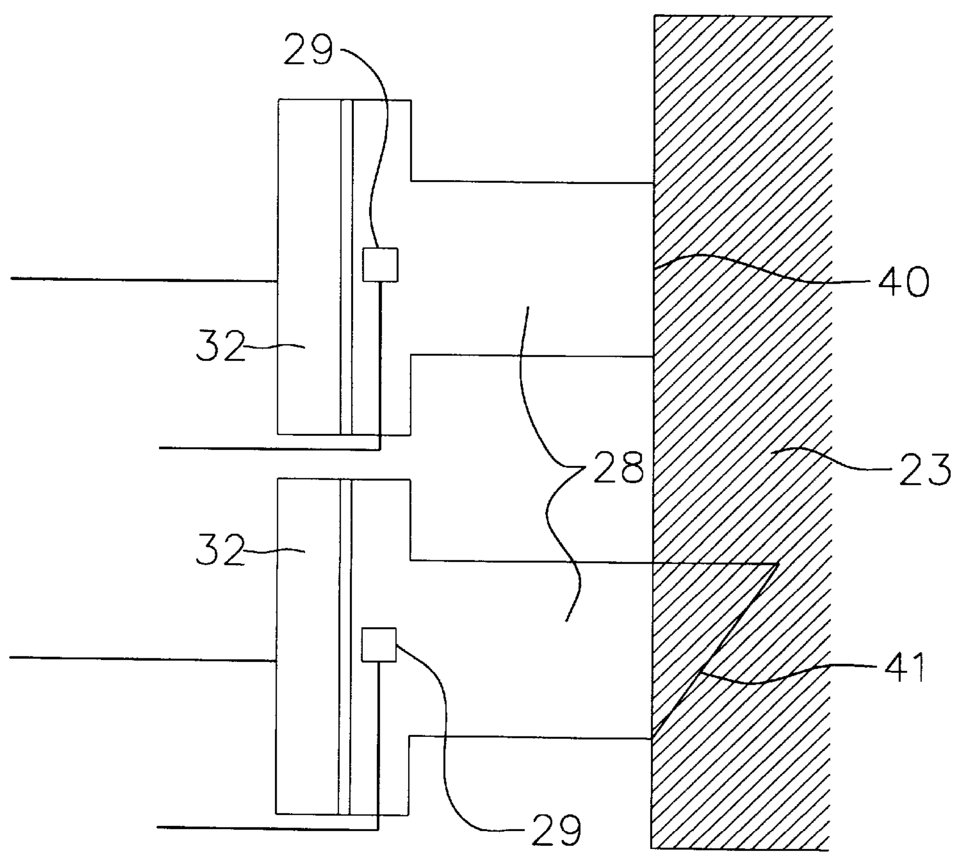
FIG. 10 shows the coupling of two LEDs in an embodiment.

Mirror coatings for the coupling mirror and the opposing mirror are not applied. FIG. 10 shows the coupling of two LEDs 28, whereby one LED has a normally designed (convex toward the outside) or a forward planar dome 40 and the other has a forward planar and oblique termination 41 for the coupling of the radiation into the measurement volume 23. The radiation is coupled directly via the LED dome into the measurement volume. The measurement module 32 behind the LED with the planar window 40 receives both photons from the measurement volume (diffuse reflection) and also photons (refractive index and absorption) specularly reflected at the dome/measurement volume boundary surface. The measurement module 32 behind the LED with an oblique planar window 41 receives, in contrast, only photons from the measurement volume, since as a result of the oblique surface, the specularly reflected photons are not directed at the receiver. The coupling of the two measurement signals thus enables synchronous determination of the absorption and diffuse reflection characteristics of the measurement volume. In another embodiment, the windows in contact with the measurement volume are provided with surfaces coated with an indicator or a substance selective layer.

Depending on the application, multiple LEDs may be in disposed, for example linearly or in drum form. In that case, the receivers installed directly on the LED basis can be replaced by an optical arrangement with downstream diode cells or a CCD camera.

In another embodiment that has the measurement volume located outside the sensor, a radiation guiding tube is mounted directly on the window or the opposing mirror. The tube containing the measurement volume to be investigated may be designed cylindrical and without an opposing mirror. The tube has a refractive index which permits a total reflection of the coupling photons and diffuse transmission photons located in the tube. Application examples are a macro-flow through cell or an optical waveguide filled with a liquid. Such an arrangement has the event each that with punctiform coupling of radiation in an extended measurement volume, the disruptive distance law $I/r^2$ has little or no effect.

In yet another embodiment, radiation guiding elements are coupled to each other. The radiation guiding element where the measurement volume is located in an opening between a coupling mirror and an opposing mirror is coupled to the radiation guiding element where the measurement volume is located outside.

Figure 11:
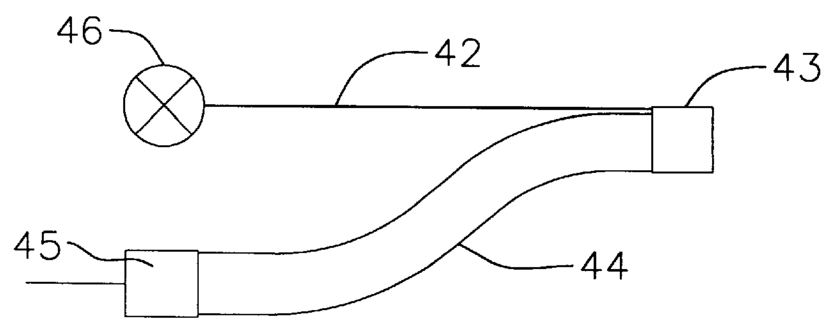
FIG. 11 shows an optical waveguide/bundle to guide transmitted coupling radiation.
Figure 12:
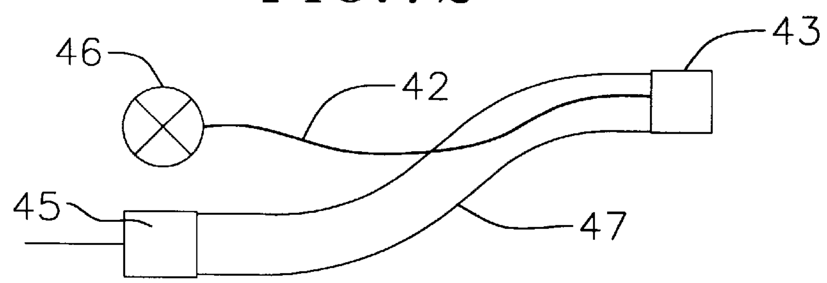
FIG. 12 shows an optical waveguide bundle for coupling and decoupling.

In other embodiments as shown in FIG. 11 and 12, coupling takes place via the semireflecting planar mirror 43 by means of optical waveguides 42, whose diameters are significantly smaller than the diameter of the coupling mirror. Only then are the radiation losses lower as a result of decoupling through the coupling optical waveguide. FIG. 11 shows an optical waveguide/bundle to guide transmitted coupling radiation 44. FIG. 12 shows an optical waveguide bundle for coupling and decoupling. The detection or decoupling of transmitted coupling radiation from the Eden multiple reflection space is realized via an optical waveguide 44 disposed downstream immediately after the coupling mirror, which brings the radiation to the receiver 45. The diameter of the optical waveguide on the coupling mirror side is equal to that of the mirror coating. In this optical waveguide can be an optical waveguide bundle. The optical waveguide heads here the function of the light guiding cone 8 in FIG. 1. The optical waveguide provided for the coupling and the optical waveguide provided for the detection of the transmitted coupling radiation can also be placed as a bundle 47 as shown in FIG. 12. The coupling may then be carried out at any non-mirrored location of the coupling mirror, e.g., centrally. Between the radiation source 46 and the optical waveguide as well as between optical waveguides and receivers, spectrally selective elements can be disposed, depending on the application.

Figure 13:
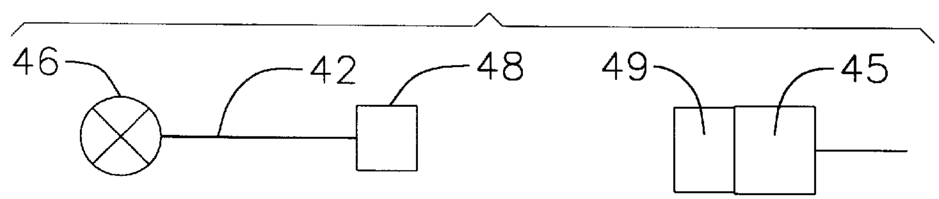
FIG. 13 shows radiation coupled through a small optical opening located in the coupling mirror via an optical waveguide.
Figure 14:
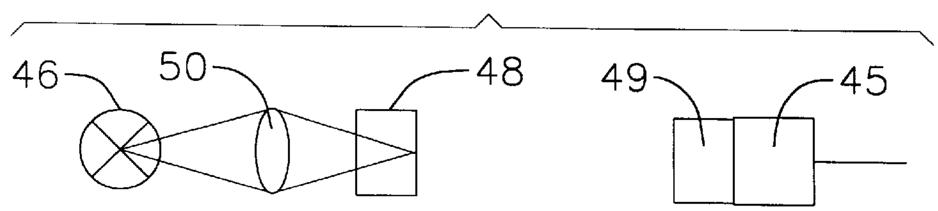
FIG. 14 shows radiation coupled through a small optical opening located in the coupling mirror via an optical system 50.

In some embodiments, as shown in FIG. 13 and 14, the coupling mirror 48 is designed as a full mirror (i.e., not semireflecting) and the opposing mirror 49 is semireflecting. The radiation is coupled through a small optical opening located in the coupling mirror. This takes place either directly via an optical waveguide 42 as shown in FIG. 13 or via an optical system 50 as shown in FIG. 14. The receiver 45 to record transmitted coupling radiation is disposed downstream from the semireflecting opposing mirror 49. Depending on the application, spectrally selective elements may be disposed between the receiver and opposing mirror as well as between the radiation source and the optical waveguide/optical system.

Figure 15:
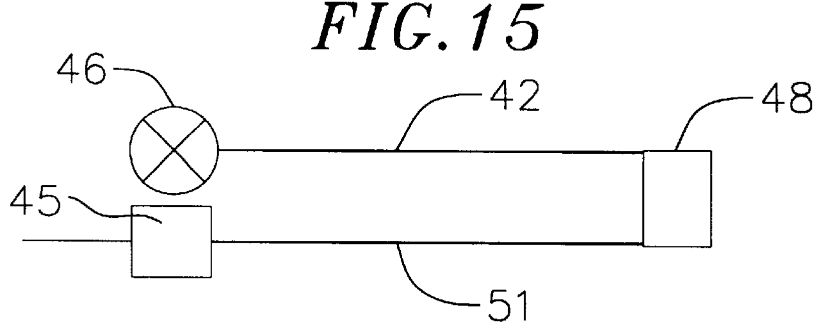
FIG. 15 shows an embodiment for decoupling the coupling radiation using a second optical waveguide, which is located at an optical opening and the coupling mirror, which is disposed downstream from the coupling mirror.
Figure 16:
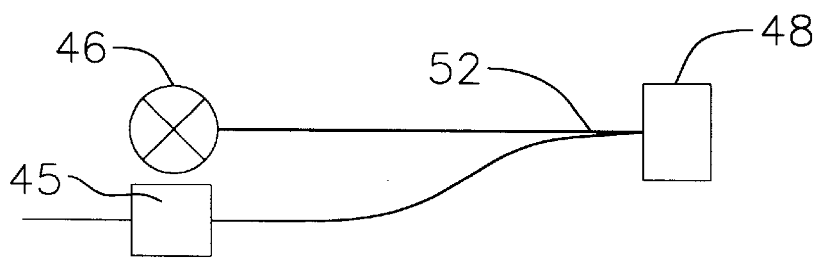
FIG. 16 illustrates the case in which coupling takes place by means of an optical waveguide branching element.
Figure 17:
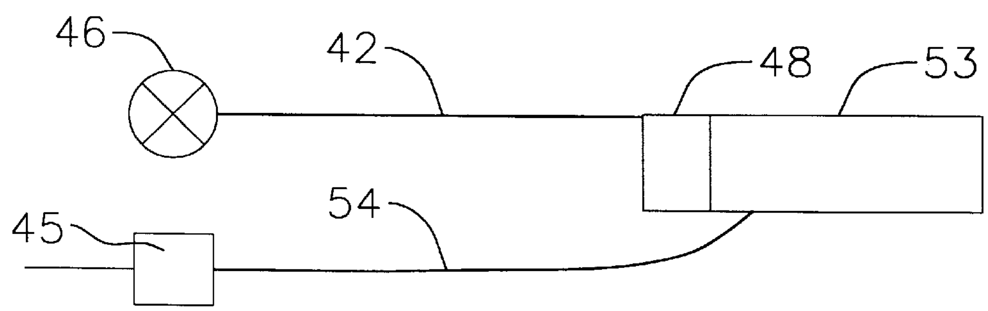
FIG. 17 shows the decoupling of coupling radiation wherein a radiation guiding volume, which has an opening in its jacket, is provided upstream from the coupling mirror.
Figure 18:
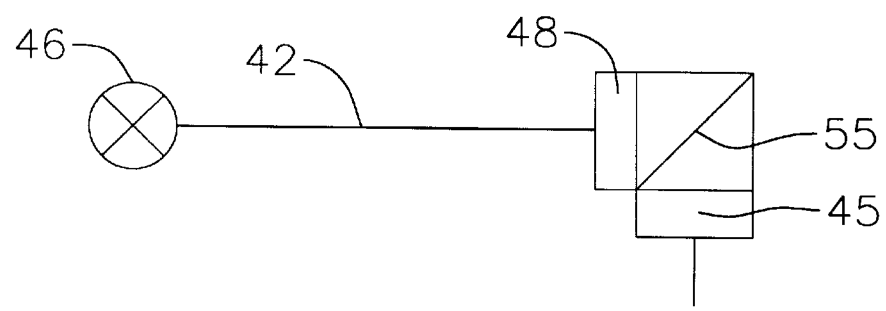
FIG. 18 illustrates another variant of the decoupling, which consists of a transmitting body, which decouples a small part of the coupling radiation out of the beam with which the receiver is irradiated, depending on the refractive index, and is installed upstream from the coupling mirror.

In some embodiments, as shown in FIG. 15, the radiation is coupled through a small optical opening located in the coupling mirror 48. This takes place either directly via an optical system or via an optical waveguide 42. To decouple coupling radiation, a second optical waveguide 51, which is located at an optical opening and the coupling mirror, is disposed downstream from the coupling mirror. FIG. 16 illustrates the case in which coupling takes place by means of an optical waveguide branching element 52. In FIG. 17, for decoupling of coupling radiation, a radiation guiding volume 53, which has an opening in its jacket, is provided downstream from the coupling mirror. Part of the radiation after each cycle can leave the radiation guiding volume through this opening. An optical waveguide 54 can be disposed downstream from this opening. This system works similar to the optical waveguide branching element. The diameter of the branching element on the coupling mirror side is the same as that of the coupling mirror. The coupling mirror may be vapor deposited on the branching element. FIG. 18 illustrates another variant of the decoupling, which consists of a transmitting body 55 (e.g., a glass plate), which decouples a small part of the coupling radiation out of the beam with which the receiver 45 is irradiated, depending on the refractive index, and is installed downstream from the coupling mirror. The reflection level of the plate is set depending on the application, e.g., through the choice of the material or through the design of defined boundary surfaces between this plate and a carrier. Instead of a plate, a radiation guiding volume with an oblique boundary surface may also be placed. Moreover, an indicator volume with defined, constant optical characteristics can be placed downstream from the coupling mirror. This volume is penetrated by the coupling radiation and delivers a measurable optical signal for the receiver, for example, as fluorescence or dispersion.

The essential characteristics of the device described are applicable not only for optical waveguides or wavelengths of the optical spectral range, but also for different wavelengths, for example: Ultrasound and nuclear radiation.

The sensor system described can either be incorporated into or added onto spectroscopic measurement technology available on the market in using the electronics included therein. Also, the sensor system can be coupled with a separate highly integrated electronic control and evaluation unit. The electronics enable both cw-operation and flash operation. In flash operation. the measurement of the dark signal is possible after each flash. A special characteristic is that depending on the optical characteristics of the measurement volume to be investigated, the sensitivity of the measurement can be electronically adjusted. For this, first, the LED current is variable, which has a direct effect on the LED intensity emitted. Secondly, the termination on the optoelectronic receivers is variable, which has direct effects on the electrical signal applied to the receiver.

What is claimed is:

1. A method for the synchronous determination of the absorption, dispersion, fluorescence, and refraction of a measurement volume having a coupling side, wherein radiation of defined wavelength is coupled into a multiple reflection device equipped with a coupling mirror on the coupling side and an opposing mirror, the method comprising:

arranging coupling radiation to fall on a measurement volume by means of the coupling mirror measuring the coupling radiation transmitted through the measurement volume after virtually complete absorption of the coupling radiation with a first receiver located immediately behind one of the two mirrors, wherein the one of the two mirrors is semireflecting;

measuring a saturated long-path diffuse reflection directed into the multiple reflection device against a direction of incidence with a second receiver directed at the measurement volume and located on the coupling mirror;

determining the absorbing power from the reciprocal value of the transmitted coupling radiation;

determining the dispersion power and the fluorescence power indirectly from the combination of saturated long-path diffuse reflection and transmitted coupling radiation;

measuring with a third receiver a second radiation generated with a second radiation source, wherein the second radiation is directed through an optical window located on the coupling side of the measurement volume, such that the second radiation is specularly reflected at a boundary surface of the measurement volume; and determining the refraction from the combination of specularly reflected radiation and transmitted coupling radiation such that a refraction index independent of the absorption of the measurement volume results.

2. The method according to claim 1 further comprising measuring an integral diffuse reflection with a receiver.

3. The method according to claim 1 wherein the absorption power determined from the transmitted coupling radiation, is determined by subtracting an intensity which is proportional to the saturated long-path diffuse reflection from the intensity of the radiation passing through the semireflecting mirror, whereby the proportionality factor is a function of the transmittance of the semireflecting mirror.

4. The method according to claim 1 wherein the dispersion and fluorescence power are determined by measuring a linear short-path diffuse reflection, which develops immediately after the coupling of the radiation incident on the measurement volume by directing an optoelectronic receiver at the part of the measurement volume located immediately at the coupling site, and calculating the quotient of the short-path diffuse reflection and the long-path diffuse reflection for the indirect determination of the absorption power.

5. The method according to claim 1 wherein the saturated long-path diffuse reflection and the linear short-path diffuse reflection are measured with time resolution and the reciprocal of the difference between the temporal widths of the two signals is used as a measure of the absorption power.

6. The method according to claim 5 wherein the measurement of the linear short-path diffuse reflection is undertaken with a short time window and the measurement of the saturated long-path diffuse reflection is undertaken with a broad time window, whereby the width of the two time windows are adjusted and determined by the respective prevailing difference between the temporal widths of the short-path and long-path diffuse reflection based on the optical thickness of the measurement volume to be investigated, in that for optically thicker measurement volumes comparatively short time windows are set and for optically thinner measurement volumes comparatively long time windows are set, and the absorption power is determined from the quotients of the signal intensities in the short and long time windows.

7. The method according to claim 1 wherein spectrally selective elements are disposed first in the absorption region of the substances to be detected and also in the absorption region of the solvent but outside the absorption region of the substances to be detected.

8. The method according to claim 1 wherein for optically thin measurement volumes, the dispersion and fluorescence power is determined directly from the linear long-path diffuse reflection and for the determination of the absorption power, the transmission after multiple reflection is determined, in that the radiation coupled into the measurement volume is decoupled out of the measurement volume after a defined path length and is directed to an optoelectronic receiver for measurement.

9. The method according to claim 1 wherein for optically thin measurement volumes, with which no saturated long-path diffuse reflection can be generated as a result of multiple reflection through the measurement volume alone, the absorption power is determined from the transmitted coupling radiation.

10. The method according to claim 1 wherein for optically thin measurement volumes, for the generation of a saturated long-path diffuse reflection and for optimization of the signal/noise relationship, the mean path length of the coupled radiation is shortened, in that artificial absorbers with defined transmission characteristics are introduced into the beam path, whereby the transmission of the absorbers is adapted to the optical thickness of the measurement volume, in that the reciprocal of the smallest possible total absorption coefficient of the measurement volume is used as a measure of the mean wavelength and consequently of the transmission of the absorbers.

11. The method according to claim 1 wherein for optically thicker measurement volumes, the coupling mirror is tilted out of the beam path and the absorption power is determined conventionally directly from the attenuated intensity and the dispersion and fluorescence power is determined directly from the linear short-path diffuse reflection.

12. The method according to claim 1 wherein the fluorescence is measured at an angle of 90° to the coupling radiation, whereby the correct fluorescence of the measurement volume and also the absorption of the measurement volume are determined by the fluorescence wavelength, in that 90° fluorescence, diffuse reflection, and transmitted coupling radiation are combined.

13. The method according to claim 1 wherein the transmitted coupling radiation and the diffuse reflection are measured at wavelengths of high and/or moderate and/or low reflectivities at comparatively low absorption of the semireflecting mirror, whereby the absorption power is determined from a parameter which is a function of the reciprocal of the transmitted coupling radiation, and the dispersion power and fluorescence power are determined indirectly from the combination of saturated long-path diffuse reflection and transmitted coupling radiation.

14. The method according to claim 13 wherein measurement volumes, with which a saturated long-path diffuse reflection is generated as a result of multiple reflection through the measurement volume alone, the spectral reflectivity of the semireflecting mirror is adapted to the spectral absorption of the measurement volume, in that the wavelength ranges of high mirror reflectivity coincide with the wavelength ranges of comparatively low absorption of the measurement volume and the wavelength ranges of low mirror reflectivity coincide with the wavelength ranges of comparatively high absorption of the measurement volume.

15. The method according to claim 13 wherein with optically thin measurement volumes the spectral reflectivity of the semireflecting mirror is adapted to the spectral absorption of the measurement volume such that the wavelength ranges of high mirror reflectivity coincide with the wavelength ranges of comparatively high absorption of the measurement volume.

16. The method according to claim 1 wherein with optically thick measurement volumes, with which a saturated long-path diffuse reflection is generated by the measurement volume alone without an opposing mirror, the measurement is performed such that instead of the opposing mirror designed as a convex mirror, one of either an optically transmissive protective window or an opposing mirror with transmitting regions is located, such that the measurement volume is located outside a multiple reflection area outside on the window or the opposing mirror and interacts with the coupling radiation.

17. The method according to claim 14 wherein with optically thick measurement volumes, the spectral reflectivity of the semireflecting coupling mirror is adapted to the spectral diffuse reflection of the measurement volume, in that the wavelength ranges of high mirror reflectivity coincide with the wavelength ranges of higher diffuse reflections of the measurement volume and the wavelength range of lower diffuse reflections of the measurement volume coincide with the wavelength ranges of low reflectivities of the semireflecting coupling mirror.

18. The method according to claim 1 wherein the coupling radiation is virtually completely absorbed as a result of long paths in a light-conducting solid located between the coupling mirror and the opposing mirror, whereby the measurement volume is in contact with the light-conducting solid such that the coupling radiation conducted through the solid can also be absorbed by the measurement volume through evanescent waves and the absorption of the measurement volume is determined from the reciprocal of the transmitted coupling radiation.

19. The method according to claim 18 wherein the diffuse reflection is measured and used for at least one of determination of the absorption of the measurement volume or correction of the transmitted coupling radiation.

20. The method accorded claim 1 wherein the radiation specularly reflected at the boundary surface with the measurement volume is measured such that a radiation source is imaged on a receiver, whereby both the imaging optics and the boundary surface are disposed in reflection geometry between the radiation source and the receiver.

21. The method according to claim 1 wherein the radiation reflected from the boundary surface with the measurement volume is separated from specular reflections of other boundary surfaces, in that the radiation source and the receiver are adjusted obliquely at an angle different from zero relative to the axis of incidence and the thickness of the optical window is set adequately high.

22. The method according to claim 1 wherein the diffuse reflections measured with the receivers aligned directly with the measurement volume are used for correct determination of the radiation intensity specularly reflected at the boundary surface with the measurement volume, in that an intensity which is proportional to the diffuse reflection caused by the measurement volume is subtracted from the radiation directed in the direction of the specular reflection.

23. The method according to claim 1 wherein in the case of approximately constant refractive indexes of the measurement volume, the radiation specularly reflected at the boundary surface is used for the detection of optical changes of the optical window, such as contamination and aging, and is combined with the diffuse reflection measured through the optical window and transmitted coupling radiation, such that a diffuse reflection independent of the changes in the window and transmitted coupling radiation result.

24. The method according to claim 1 wherein a receiver, which measures an intensity, which includes both diffuse reflection photons and specularly reflected radiation, which are combined for the determination of the refraction with the diffuse reflection and the transmitted coupling radiation, is disposed between the two diffuse reflection receivers.

25. The method according to claim 1 wherein the measurement volume includes flowing material, the rate of flow of which is determined optically, the method further comprising:

determining cumulatively one of reflectance or diffuse reflection in a relatively large and defined measurement time interval as integral diffuse reflection, such that this depends on the inherent absorption, dispersion, and fluorescence power as well as the refractive power of the measurement volume and the rate of flow of the material of the measurement volume;

determining a diffuse reflection in a relatively short time as a differential diffuse reflection, such that it depends exclusively on the inherent absorption, dispersion, and fluorescence power as well as the refractive power; and combining the two diffuse reflection signals such that one value results, which depends exclusively on the rate of flow of the material of the measurement volume.

26. A spectroscopy device comprising:

a module system having an absorption module, a diffuse reflection module and a refraction module; and a reflection module connected to and disposed opposite the module system; wherein the absorption module includes a coupling module, a measurement module, an optical waveguide module, and a connection module wherein a plurality of optical waveguides are disposed in the coupling module and are aligned parallel to the normal of a coupling mirror, whose end faces responsible for the light output form a common straight line and a common vertical plane, a semireflecting coupling mirror is coated on the back with a semireflecting coat and a nonreflecting region is located between the mirror jacket and the mirror coating, on which region the end faces of the optical waveguides lie flat and form a common vertical plane with the mirror coating, as well as for the purpose of passing on the coupling radiation transmitted by a measurement volume and passing through the semireflecting coupling mirror, a conically designed radiation guiding volume is disposed between the receiver with a relatively small surface and the reflecting region of the semireflecting coupling mirror with a relatively large surface located in the measurement module, as well as the optical waveguides brought out of the coupling module are guided farther along a defined path in an optical waveguide module directly connected to the coupling module such that their end faces responsible for the light entry are positioned in a common vertical plane and the light emitting diodes likewise located in a common vertical plane connection module directly connected to the optical waveguide module and are positioned directly opposite an optical waveguide, which is used for the transmission of radiation of a radiation source located outside the module system, as well as various types of reflection modules equipped with opposing mirrors are coupled with the absorption module.

27. The method according to claim 1 further comprising:

measuring dispersion and fluorescence with two optoelectronic receivers; and suppressing the dispersion or fluorescence radiation with filters disposed downstream from the receiver directed at the measurement volume for selective determination of the dispersion and fluorescence component of the diffuse reflection.

28. The method according to claim 1 wherein for optically thicker measurement volumes, the opposing mirror is replaced by an optoelectronic receiver and the absorption power is determined conventionally directly from the attenuated intensity and the dispersion and fluorescence power is determined directly from the linear short-path diffuse reflection.

29. The spectroscopy device according to claim 26 wherein the measurement volume is located in a second radiation guiding volume including reflecting jacket surfaces and end faces responsible for light entry and output.

30. The spectroscopy device according to claim 24 wherein the measurement volume is located outside a second radiation guiding volume, but is in contact with the coupling radiation.

* * * * *